(12) United States Patent
Annis

(10) Patent No.: US 6,993,111 B1
(45) Date of Patent: Jan. 31, 2006

(54) METHOD AND APPARATUS FOR IMPROVING THE SPATIAL RESOLUTION OF A LAMINOGRAPHY SYSTEM THAT EMPLOYS AN X-RAY SOURCE WITH A SCANNING BEAM

(76) Inventor: Martin Annis, 66 Church St., Cambridge, MA (US) 02138

( * ) Notice: Subject to any disclaimer, the term of this patent is extended or adjusted under 35 U.S.C. 154(b) by 0 days.

(21) Appl. No.: 11/059,966

(22) Filed: Feb. 17, 2005

Related U.S. Application Data

(60) Provisional application No. 60/544,965, filed on Feb. 17, 2004.

(51) Int. Cl.
*G01N 23/04* (2006.01)

(52) U.S. Cl. .......................... 378/57; 378/69
(58) Field of Classification Search ................. 378/57, 378/12, 26, 146, 68–69, 205
See application file for complete search history.

(56) References Cited

U.S. PATENT DOCUMENTS 6,453,007 B2 * 9/2002 Adams et al. ................. 378/90
6,628,745 B1 * 9/2003 Annis et al. .................. 378/21

* cited by examiner

*Primary Examiner*—David V. Bruce
*Assistant Examiner*—Hoon Song
(74) *Attorney, Agent, or Firm*—Altman & Martin

(57) ABSTRACT

A method and apparatus for reducing blurring caused by transverse movement of an object being inspected relative to the x-ray source/detector array assembly. The plane of the scanning fan beam plane generated by the x-ray source is tilted by an angle relative to the plane that is perpendicular to the direction of motion of the object by an angle such that the fan beam source traverses distance D parallel to the direction of motion of the object in the same amount of time as one scan of the fan beam.

1 Claim, 4 Drawing Sheets

METHOD AND APPARATUS FOR IMPROVING THE SPATIAL RESOLUTION OF A LAMINOGRAPHY SYSTEM THAT EMPLOYS AN X-RAY SOURCE WITH A SCANNING BEAM

CROSS-REFERENCES TO RELATED APPLICATIONS

The applicant wishes to claim the benefit of U.S. Provisional Patent Application No. 60/544,965, filed Feb. 17, 2004 for SPATIAL RESOLUTION BY TILTING DETECTOR/X-RAY SOURCE PLANE in the name of Martin Annis.

STATEMENT REGARDING FEDERALLY SPONSORED RESEARCH OR DEVELOPMENT

Not Applicable

REFERENCE TO A SEQUENCE LISTING, A TABLE, OR A COMPUTER PROGRAM LISTING COMPACT DISK APPENDIX

Not Applicable

BACKGROUND OF THE INVENTION

1. Field of the Invention

The present invention relates to laminography and more particularly to a method and apparatus for reducing the blurring of the images obtained using an x-ray source with a traveling x-ray beam.

2. Description of the Related Art

U.S. Pat. No. 6,628,745, issued to the present applicant, describes a Laminography inspection system. As shown in FIGS. 1 and 2, an x-ray source 12 uses a narrow pencil beam 24 of high-energy electrons from a DC source of electrons 20 through a vacuum chamber 30 and directed to a linear target 22. A magnetic deflector 28 deflects the electron beam 24 so that it scans in an x-ray source line 52 along the linear target 22, as at 40, striking the target 22 continuously along the x-ray source line 52. An x-ray cone beam 16 is produced where the electron beam 24 strikes the target 22. This x-ray cone beam source 26 moves continuously to produce a moving cone beam 16 along the x-ray source line 52. The x-ray cone beam 16 exits the vacuum chamber 30 through a thin window located at the top of the vacuum chamber 30 just below a slit collimator 34. The collimator 34 produces a fan beam 32 from the cone beam 16. The fan beam 32 is directed to the object being inspected 2 in a direction transversely perpendicular to the direction of travel 4 of the object 2. X-rays passing through the object 2 are detected by a U-shaped or L-shaped linear detector array 14 in the plane 44 of the fan beam 32. The object 2 moves continuously on a conveyor 6 while the x-ray cone beam 16 scans from one end of the x-ray source line 52 to the other. This means that the object 2 is blurred transversely by the distance that the object 2 moves during the passage of the x-ray cone beam 16 from one end of the source line 52 to the other. For example, if the object moves 2 mm during the 800 mm travel of the x-ray cone beam, the blurring is 2 mm.

The application of the invention to CT systems is limited to the CT systems covered by U.S. patent application Ser. No. 10/630,364, incorporated herein by reference.

BRIEF SUMMARY OF THE INVENTION

An object of the present invention is to improve the spatial resolution of prior art Laminography systems by a simple change to the geometry of the system.

The present invention is a method and apparatus for reducing blurring caused by transverse movement of the object being inspected relative to the x-ray source 12/detector array. The amount of blurring is the distance D the object travels during the time T it takes for one scan of the x-ray source line. In the present invention, the fan beam plane is tilted by an angle relative to the plane that is perpendicular to the direction of motion of the object. The angle of the fan beam plane is chosen so that the x-ray cone beam source traverses distance D parallel to the direction of motion of the object in the same amount of time as one scan of the x-ray source line of length L. The required angle θ is quite small and is $\theta=\sin^{1}(D/L)$. In the typical Laminography system, the distance D is the width of one detector pixel and the angle is such that one end of the x-ray source line is offset by one detector pixel width from the other end of the x-ray source line.

Other objects of the present invention will become apparent in light of the following drawings and detailed description of the invention.

BRIEF DESCRIPTION OF THE DRAWINGS

For a fuller understanding of the nature and object of the present invention, reference is made to the accompanying drawings, wherein.

DETAILED DESCRIPTION OF THE INVENTION

The present invention is a method and apparatus for reducing blurring caused by transverse movement 4 of the object being inspected 2 relative to the x-ray source 12/detector array 14 assembly during the time it takes for the x-ray cone beam 16 to travel the length of the x-ray source line 52.

Figure 1:
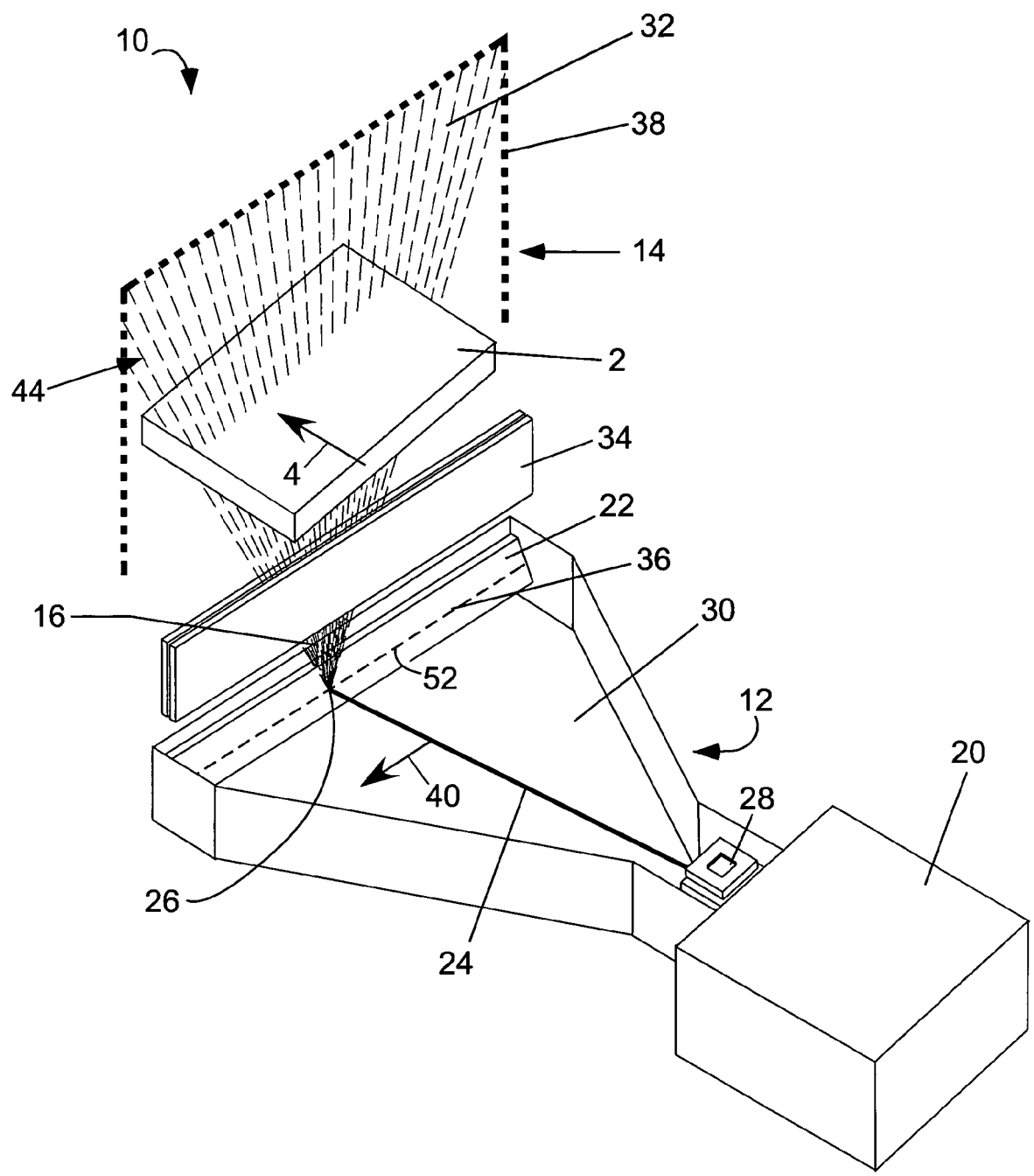
FIG. 1 is a perspective diagram of a Laminography system with which the present invention can be employed.
Figure 2:
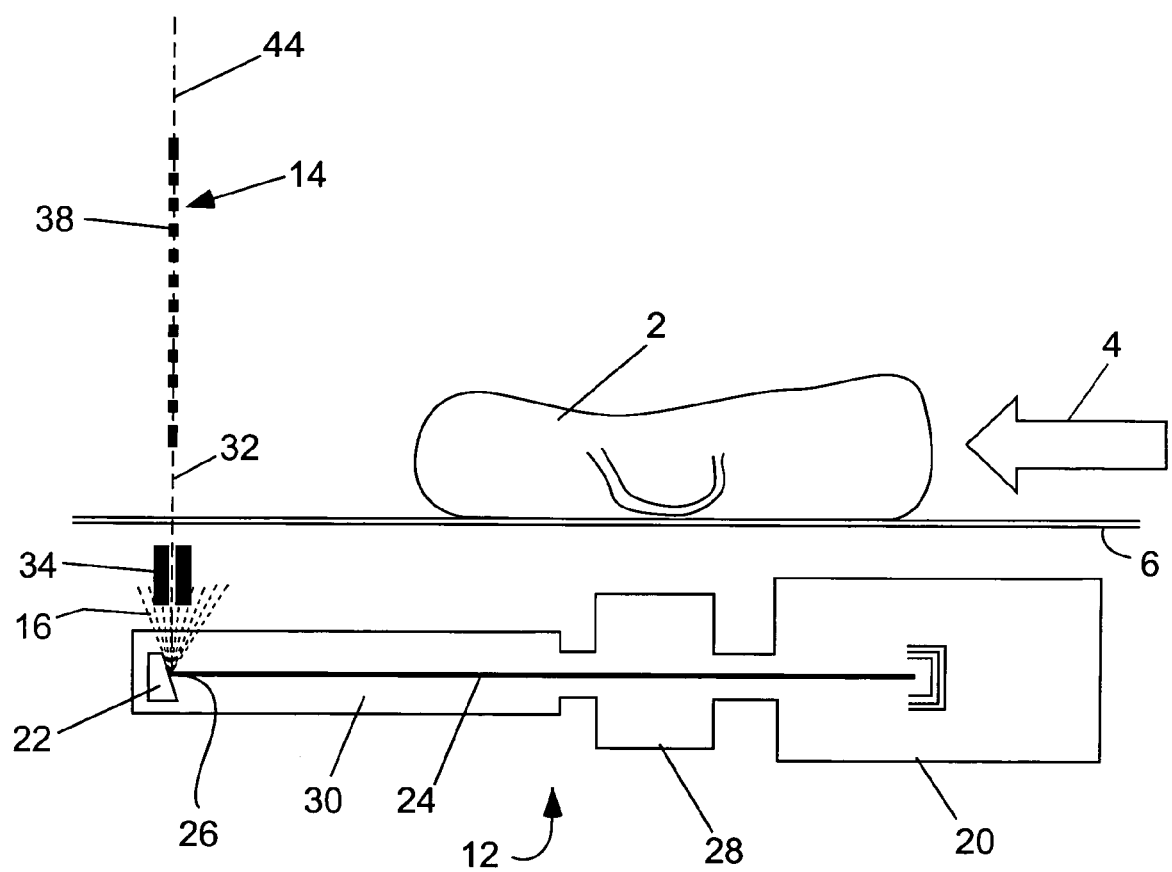
FIG. 2 is a cross-sectional diagram of the Laminography system of FIG. 1.
Figure 3:
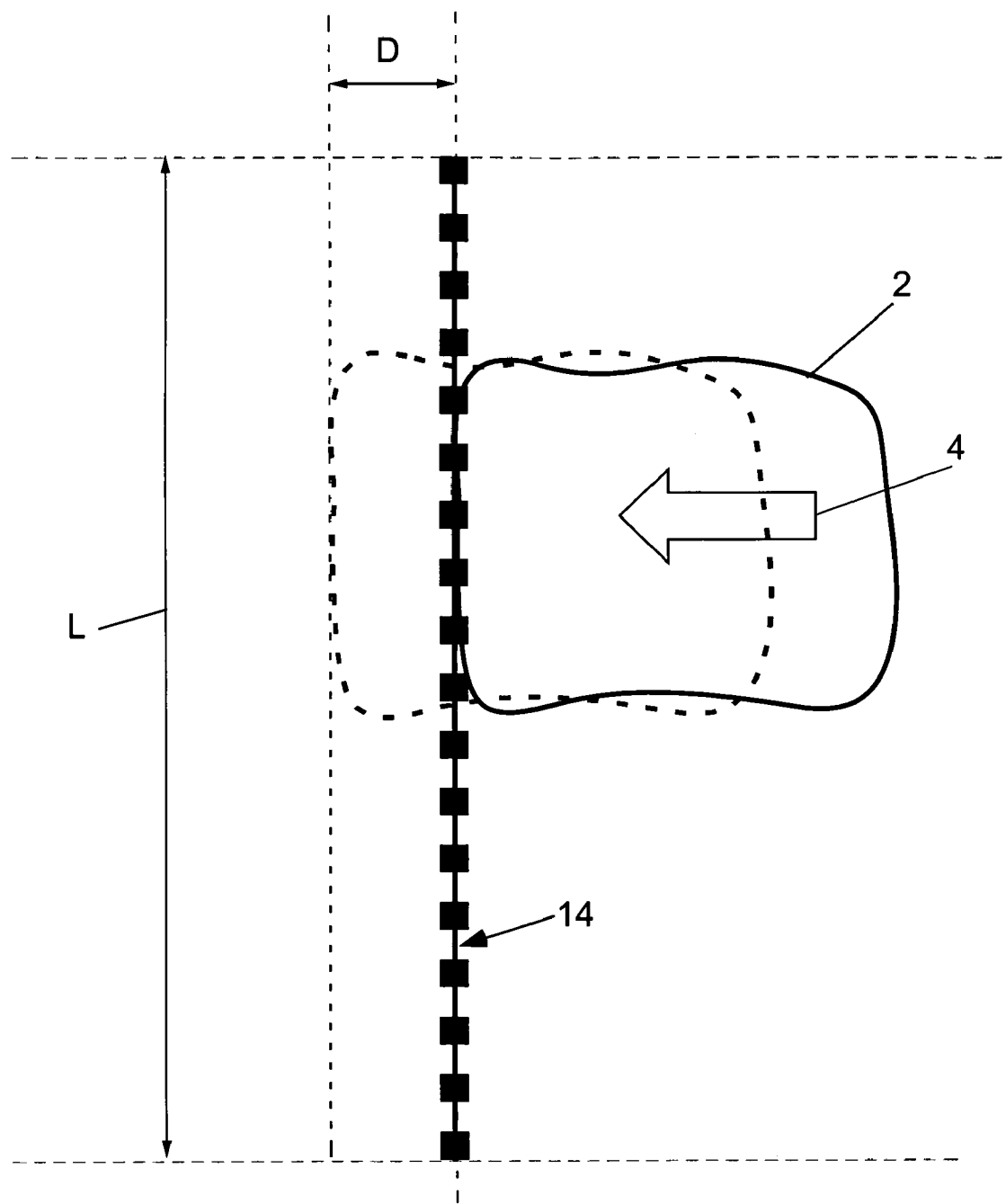
FIG. 3 is a cross-section of the object region of a conventional Laminography system of FIG. 1.

A Laminography system 10 incorporating the present invention is shown in FIGS. 1 and 2 and is described above. As shown in FIG. 3, a vertical slice 42 through the object 2 moves the distance D as the x-ray cone beam source 26 scans the length L from one end of x-ray source line 52 to the other. D is determined by multiplying the speed of the object S by the x-ray source scan time T, the time the x-ray cone beam source 26 takes to scan from one end of x-ray source line 52 to the other, that is, D=S*T. For example, in a typical system, the speed S of the object 4 is 100 mm/sec and the cone beam source scan time T is 20 msec. Thus, the object 2 travels 100 mm/sec*20 msec=2 mm during a single cone beam source scan.

Figure 4:
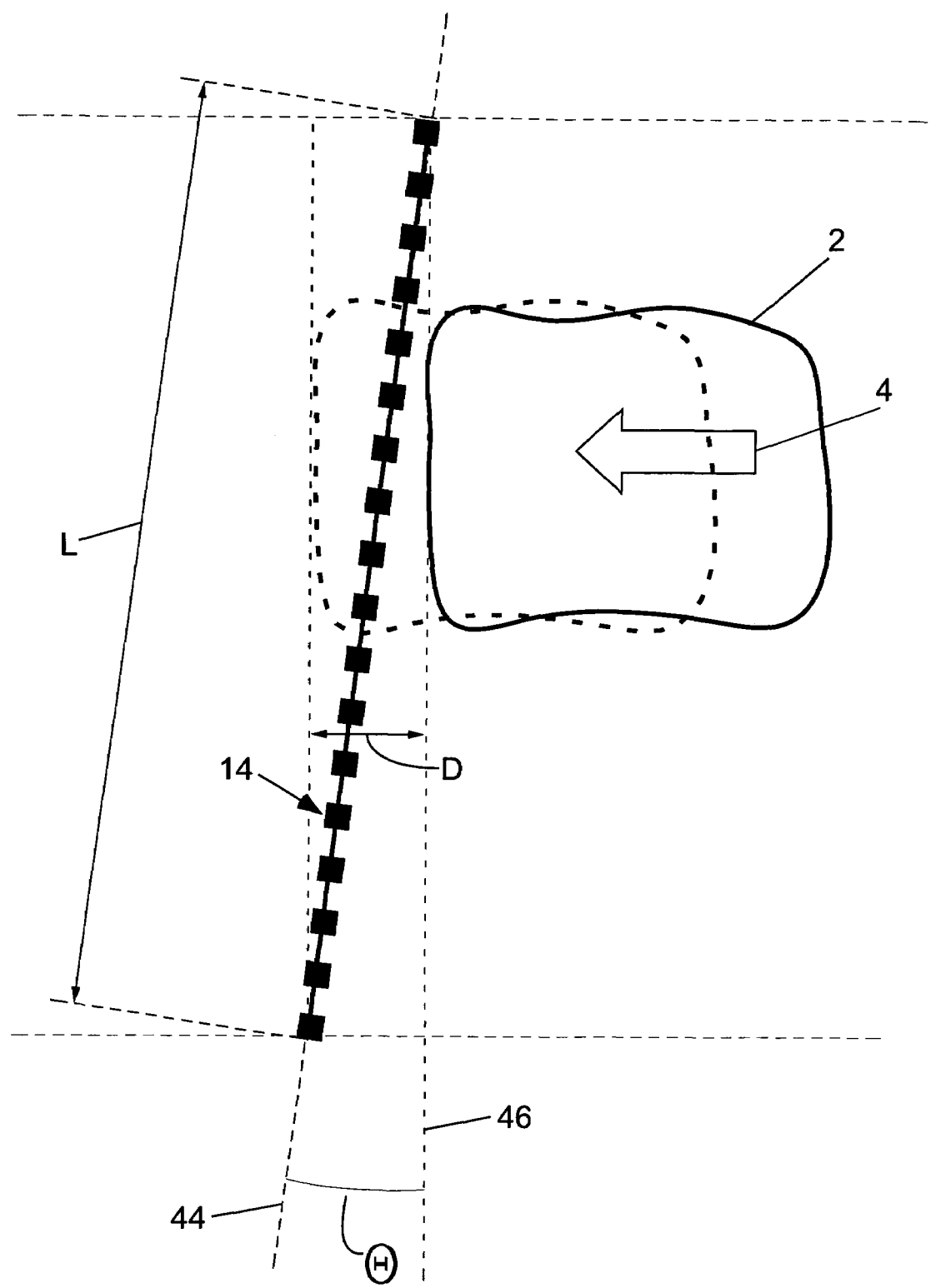
FIG. 4 is a cross-section of the object region of a Laminography system of FIG. 1 employing the present invention.

In the present invention, the fan beam plane 44, which is defined by the detector array and the x-ray source line 14 and which is coincident with the detector array plane, is tilted by a small angle relative to the plane that is perpendicular to the direction of motion 4 of the object 2 so that the fan beam plane 44 is not perpendicular to the plane 46 that is perpendicular to the direction of motion 4 of the object 4, as shown in FIG. 4. The angle θ of the fan beam plane 44 is chosen so that the x-ray cone beam source 26 traverses distance D in the direction of motion 4 of the object 2 in the same amount of time that it traverses length L. In other words, assuming a right triangle with the x-ray source line 52 as the hypotenuse, the side that is parallel to the direction of motion 4 of the object is the same length as the distance D traversed by the object during one scan.

The region of the object 2 that is closest to the x-ray cone beam source 26 as the object 2 moves through the system 10 is very well blurred. The region of the object 2 that is close to the detector array 14 at the top is blurred about as well as in the usual geometry. The net effect of the tilted fan beam plane 44 of the present invention is an improvement of about a factor of two in spatial resolution in Laminography imaging. Current laminography systems sample a vertical plane that is fixed in space while the object moves by one pixel transversely, thus blurring the image over the transverse pixel distance. This blurring is reduced by about a factor of two by sampling the detectors, continuously, at the location of a moving vertical plane that is between the vertical plane at the beginning of the scan and the vertical plane at the end of the scan.

The angle θ required to achieve the desired result is quite small and is $\theta=\sin^{-1}(D/L)=\sin^{-1}((S*T)/L)$. Continuing the example above, if the x-ray source length L is 800 mm, the tilt angle $\theta=\sin^{-1}(D/L)=\sin^{-1}(2\,mm/800\,mm)=0.14°$.

The typical Laminography system is designed so that the object 2 travels the width of one detector pixel 38 in the time it takes for one scan of the x-ray source line 52, that is, the distance D the object 2 travels during one scan of the x-ray source line 52 is the same as the width of a detector pixel 38. Thus, in the typical system, one end of the x-ray source line 52 is offset by one detector pixel width from the other end of the x-ray source line 52. This offset is usually easily accomplished within the existing adjustments of the typical prior art system.

With respect to computed tomography (CT) using three x-ray sources and three U-shaped x-ray detector arrays, there is a fortuitous result that allows each of the arrays to be tilted exactly as above for Laminography. (In contrast, use of a single x-ray source that surrounds the object by 180° and a 360° detector array does not permit the tilting arrangement of the present invention.) The advantage of the present invention in CT may be greater than for Laminography, because the blurring is compounded by the need to combine the data from the three source/detector assemblies.

Thus it has been shown and described a method an apparatus for improving the spatial resolution of Laminography and CT systems which satisfies the objects set forth above.

Since certain changes may be made in the present disclosure without departing from the scope of the present invention, it is intended that all matter described in the foregoing specification and shown in the accompanying drawings be interpreted as illustrative and not in a limiting sense.

I claim:

1. A system for inspecting an object having a direction of motion and a speed S in said direction of motion, said system having an improved spatial resolution and comprising:
  (a) an electron source that provides a pencil beam of electrons;
  (b) an electromagnet assembly that receives said pencil beam of electrons and that directs said pencil beam to form a scanning beam;
  (c) a linear target that is struck by said scanning beam along an x-ray source line and producing x-ray cone beams from x-ray cone beam sources in said x-ray source line when struck by said electron scanning beam, said x-ray source line having a length L and said scanning beam moving said length L in time T;
  (d) a slit collimator that receives said x-ray cone beams and emits x-ray fan beams in a fan beam plane that is tilted relative to a plane that is perpendicular to said direction of motion by an angle $\theta=\sin^{-1}(S*T)/L$);
  (e) an array of x-ray detectors in said fan beam plane that detects said x-ray fan beams as detected x-rays and provides signals corresponding to the flux intensity of said detected x-rays; and
  (f) a processor that receives said signals and produces images of selected planes through said object.

* * * * *